United States Patent
Passaniti et al.

(10) Patent No.: US 11,531,016 B2
(45) Date of Patent: Dec. 20, 2022

(54) METHOD OF OPERATING GAS SENSORS AND CORRESPONDING DEVICE, SENSOR AND PROGRAM PRODUCT

(71) Applicant: STMicroelectronics S.r.l., Agrate Brianza (IT)

(72) Inventors: Fabio Passaniti, Syracuse (IT); Enrico Rosario Alessi, Catania (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 506 days.

(21) Appl. No.: 16/565,379

(22) Filed: Sep. 9, 2019

(65) Prior Publication Data
US 2020/0088705 A1 Mar. 19, 2020

(30) Foreign Application Priority Data

Sep. 13, 2018 (IT) .................. 102018000008561

(51) Int. Cl.
  *G01N 33/00* (2006.01)
  *G01N 27/04* (2006.01)
(52) U.S. Cl.
  CPC ..... *G01N 33/0073* (2013.01); *G01N 33/0016* (2013.01); *G01N 27/04* (2013.01)
(58) Field of Classification Search
  CPC .......... G01N 33/0073; G01N 33/0016; G01N 27/04; G01N 27/124; G01N 27/123
  See application file for complete search history.

(56) References Cited

U.S. PATENT DOCUMENTS 4,567,475 A    1/1986  Bukowiecki et al.
5,517,182 A *  5/1996  Yasunaga ............. G01N 27/124
                                               73/31.06
(Continued)

FOREIGN PATENT DOCUMENTS

DE    19959925 C2 *  9/2003  ........... G01N 27/124
EP    0 853 240 A2    7/1998
(Continued)

OTHER PUBLICATIONS

Yoshikawa In view of "Sears": Sears, W. M., et al. "Selective thermally cycled gas sensing using fast Fourier-transform techniques." Sensors and Actuators B: Chemical 2.4 (1990): 283-289. (Year: 1990).*

(Continued)

*Primary Examiner* — Daniel S Larkin
*Assistant Examiner* — Fatemeh Esfandiari Nia
(74) *Attorney, Agent, or Firm* — Seed IP Law Group LLP

(57) ABSTRACT

A method includes applying heat to a metal oxide sensing element of a gas sensor, varying the heat applied to the metal oxide sensing element for at least a time interval, and measuring an electrical resistance of the metal oxide sensing element versus variation of the heat for a time interval. The measurement of electrical resistance of the metal oxide sensing element versus variation of the heat applied to the metal oxide sensing element is compared to a set of corresponding reference measurements associated with a plurality of different target gases. A further sensor parameter versus the variation of electrical resistance and variation of the heat applied is measured to obtain a three-dimensional trajectory corresponding to variation of the sensor resistance, the variation of said heat and the variation of the further sensor parameter. This comparing includes compar- (Continued)

ing the trajectory in three dimensions to a set of reference three-dimensional objects.

21 Claims, 8 Drawing Sheets

(56) References Cited

U.S. PATENT DOCUMENTS

| | | | | |
|---|---|---|---|---|
| 6,277,268 | B1* | 8/2001 | Khesin | G01N 27/407 |
| | | | | 204/429 |
| 2002/0029770 | A1* | 3/2002 | Heffel | F02D 19/087 |
| | | | | 123/527 |
| 2018/0292338 | A1* | 10/2018 | Liu | G01N 27/04 |
| 2020/0292480 | A1* | 9/2020 | Chrimes | G01N 27/124 |

FOREIGN PATENT DOCUMENTS

| | | | |
|---|---|---|---|
| JP | 7-311170 A | | 11/1995 |
| JP | 07311170 A | * | 11/1995 |
| JP | H03233699 A | * | 12/1998 |
| WO | 2007/117156 A1 | | 10/2007 |

OTHER PUBLICATIONS

Abdullah et al., "Fabrication and Testing of $SnO_2$ Thin Films as a Gas Sensor," *Archives of Applied Science Research* 4(3):1279-1288, 2012.
Gosangi et al., "Active Temperature Programming for Metal-Oxide Chemoresistors," *IEEE Sensors Journal* 10(6)): 1075-1082, 2010.
Heilig et al., "Gas identification by modulating temperatures of $SnO^2$-based thick film sensors," *Sensors and Actuators B* 43:45-51, 1997.
Lee et al., "Temperature modulation in semiconductor gas sensing," *Sensors and Actuators B* 60:35-42, 1999.
Liu et al., "A Survey on Gas Sensing Technology," *Sensors* 12:9635-9665, 2012.
Nakata et al., "Gas Sensing Based on a Nonlinear Response: Discrimination between Hydrocarbons and Quantification of Individual Components in a Gas Mixture." *Ana. Chem.* 68(13):2067-2072, 1996.
Zhang et al., "A Method of Feature Extraction From the Desorption Part of MOX's Response Curves to Gases," *IEEE Sensors Journal.* 8(11):1816-1823, 2008.
Chutia et al., "Best Frequency for Temperature Modulation of Tin Oxide Gas Sensor for Chemical Vapor Identification," International Journal of Engineering and Technology 6(2): 1158-1166, April-May 2014,.

* cited by examiner

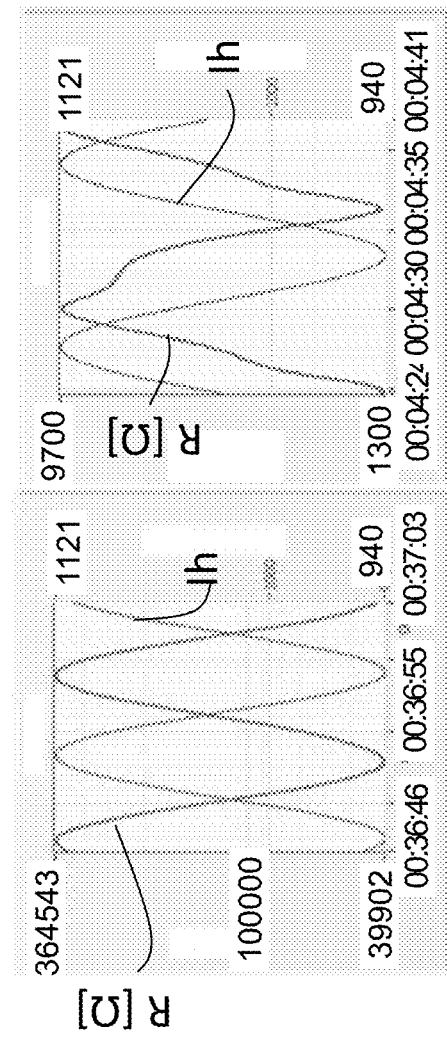
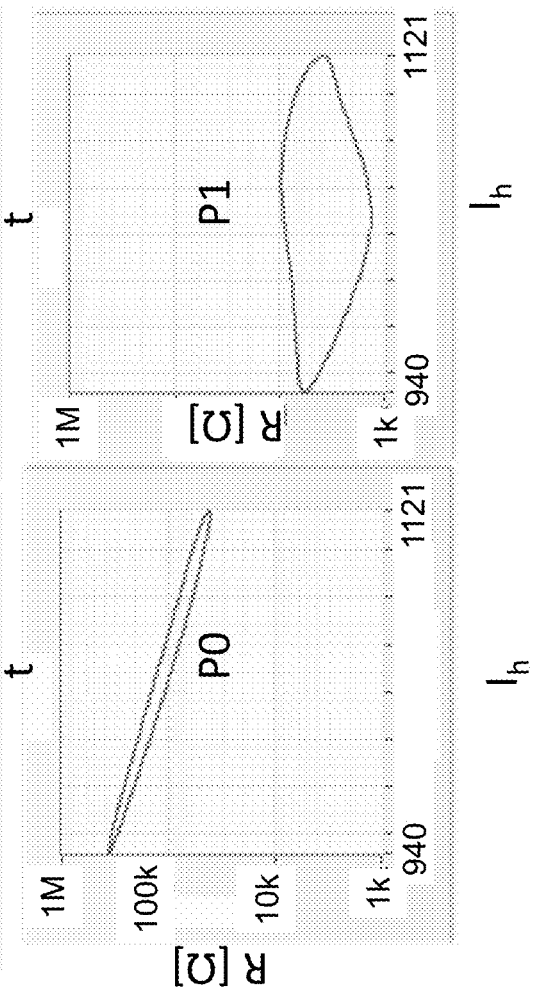

METHOD OF OPERATING GAS SENSORS AND CORRESPONDING DEVICE, SENSOR AND PROGRAM PRODUCT

TECHNICAL FIELD

The description relates to enhancing selectivity to target gases of gas sensors. Gas sensors such as Metal Oxide (MOX)-based gas sensors are exemplary of gas sensors to which embodiments may be applied.

The sensing elements may be used for detection of target gases, e.g., volatile organic compounds (VOC), such as benzene, methane, ethanol and other volatile organic compounds.

One or more embodiments relate to a gas sensor arranged on low-power, low-latency devices, e.g., portable devices such as mobile phones, handled devices or wearable devices, which may be used for air quality detection in closed environments such as homes or vehicles.

One or more embodiments apply to the field of environmental sensors in the consumer, automotive, industrial and medical markets.

BACKGROUND

Description of the Related Art

Metal Oxide (MOX) gas sensors, in particular Metal Oxide Semiconductor (MOS) gas sensors may be applied to various industrial fields, and may comprise low cost sensors with respect to devices based on different sensing technologies. MOX gas sensors may exhibit one or more advantages, e.g., a power reduction and low noise with respect to other types of gas sensors. However, they may also exhibit the disadvantage of limited selectivity.

Due to such limited selectivity, MOX gas sensor technology may be discarded for applications wherein gas type recognition is desirable.

Metal oxide, e.g., ZnO2, gas sensors may be based on a micro hot plate cyclically (e.g., continuously) heated up to 450° C. for allowing the sensing material (MOS) to be reactive in presence of volatile organic compounds (VOC) such as ethanol, toluene, benzene and formaldehyde.

The resistance of the MOX sensing material changes as a function of the gas concentration level (ppm), with the VOC concentration that may be computed as a function of the variation of the MOS resistance in presence of a VOC with respect to the MOX resistance in clean air. In order to do so, a calibration at factory level of the MOX sensing material may be operated, at the specific working conditions, that may enable translation of a ratio between MOX resistance in presence of a VOC and MOX resistance in clean air into a measure of gas concentration (ppb or ppm).

In case of applications having power consumption constraints, intermittent heating of the micro hot plate may represent an approach used for addressing such limitation. The pulse intensity and pulse width of a heating profile may be tuned according to a trade-off between power consumption and performance of the gas sensor, e.g., accuracy, sensitivity and stability. For example, known sensing technologies utilized for gas detection as described in Xiao Liu et al.: "A Survey on Gas Sensing Technology," Sensors 2012, 12, 9635-9665; doi:10.3390/s120709635.

A way to control such kind of gas sensors, either in continuous or pulsed working modes, may be to employ an additional circuit on a printed circuit board (PCB), which is able to:

set the right operating temperature of the sensor heater, by driving it with the proper current amplitudes and profiles;

acquire, condition and measure the MOS sensing resistance;

eventually compensate interfering and influencing factors (e.g., temperature, humidity);

provide an estimation of the VOC concentration.

It is well known that the main drawback of MOS sensors is a lack of selectivity. For this reason, generally, MOX based gas sensors are used for getting only an indication of air quality based on total VOC (t-VOC) measurements.

However, it is known to use a temperature modulation approach. This approach is known by publications such as:

Satoshi Nakata, Sumiko Akakabe, Mie Nakasuji, and Ken-ichi Yoshikawa "Gas sensing based on a nonlinear response: Discrimination between hydrocarbons and quantification of individual components in a gas mixture." Analytical Chemistry, 68(13):2067-2072, 1996;

U.S. Pat. No. 4,567,475 B1;

Shunping Zhang, Changsheng Xie, Dawen Zeng, Huayao Li, Zikui Bai, and Shuizhou Cai, *A Method of Feature Extraction From the Desorption Part of MOS's Response Curves to Gases*; IEEE SENSORS JOURNAL, VOL. 8, NO. 11, NOVEMBER 2008; and Rakesh Gosangi and Ricardo Gutierrez-Osuna, Senior Member, IEEE., IEEE SENSORS JOURNAL, VOL. 10, NO. 6, JUNE 2010 Active Temperature Programming for Metal-Oxide Chemoresistors.

In the latter is shown that modulating the operating temperature of metal-oxide chemical sensors gives rise to gas-specific signatures that provide a wealth of analytical information.

However, also such signatures can be similar at different gas concentrations, even in case of different gases, and this can lead to misleading results.

BRIEF SUMMARY

One or more embodiments overcome at least some of such disadvantages, and may be achieved by means of a method having the features set forth in the following.

One or more embodiments include a corresponding device, e.g., a portable device including a MOX gas sensor.

One or more embodiments relate to methods of operating a gas sensor, in particular for enhancing the selectivity of a metal oxide gas sensor.

In one embodiment, a method of operating a gas sensor, in particular to enhance the selectivity of a metal oxide gas sensor, includes:

applying heat by a heater to a metal oxide sensing element of a gas sensor varying the heat applied by said heater to said metal oxide sensing element, measuring at least an electrical resistance of said metal oxide sensing element of the gas sensor versus said variation of the heat applied to the metal oxide sensing element, and comparing said measurement of at least the electrical resistance of said metal oxide sensing element versus said variation of the heat applied to the metal oxide sensing element to corresponding reference measurements associated with a plurality of different target gases.

One or more embodiments relate to methods wherein said further sensor parameter is proportional to a gas concentration.

One or more embodiments relate to a method wherein said operation of measurement of a three-dimensional hysteretic trajectory includes a step of acquisition of the sensor resistance measured at the beginning of said modulation as a further sensor parameter, and a step in which the gas sensor resistance versus the variation of heating current is measured. The resistance of said metal oxide sensing element of the gas sensor versus a variation of the heat is obtained by modulating said heat in time and said further sensor parameter is a sensor resistance measured before performing said variation of the heat.

One or more embodiments relate to a method wherein said variation of the heat is a sinusoidal modulation.

One or more embodiments relate to a method wherein said reference three-dimensional object is obtained by a previous characterization phase where the resistance of the gas sensor is measured at different levels of concentration at selected operating conditions.

One or more embodiments relate to a method wherein said comparing said trajectory to one or more reference three-dimensional objects in said three dimensions includes recognizing said trajectory in the surface of the three-dimensional object.

One or more embodiments relate to a method wherein said comparing said trajectory to one or more reference three-dimensional objects is performed by statistical methods or by an expert system, in particular an Artificial Neural Network.

One or more embodiments relate to a method wherein said heat is measured by measuring a current applied to the heater.

One or more embodiments relate to a method wherein includes
measuring a gas sensor resistance, checking the presence of a gas by measuring a variation in time of said gas sensor resistance,
when variation in time of said gas sensor resistance matches a stationarity criterion,
performing at least said operation of measurement of a three-dimensional hysteretic trajectory and said comparing operation.

One or more embodiments relate to a method wherein, once the target gas is recognized, a step of controlling an actuation system is performed on the basis of the information on the recognized target gas.

One or more embodiments relate to a method wherein at least one following operation is performed:
the gas sensor is driven for changing the operating mode in order to be more sensitive to the recognized gas;
the gas sensor is driven for changing the operating mode in order to be less sensitive to the recognized gas.

One or more embodiments also relate to a circuit, comprising:
at least one input node configured to receive from a sensor a sensing signal indicative of a sensed entity,
at least one power node configured to power the sensor,
processing circuitry, coupled with the at least one input node and the at least one power node the processing circuitry configured to perform the steps of the method according one of the above embodiments.

One or more embodiments also relate to a device, comprising:
at least one sensor, preferably a gas sensor, still more preferably a metal oxide semiconductor gas sensor, producing a sensing signal indicative of sensed entity,
a circuit according to the above embodiment, arranged with said at least one input node coupled to the sensor to receive said sensing signal therefrom and said at least one power node coupled to the sensor for powering the sensor.

One or more embodiments also relate to a computer program product, loadable in the memory of said processing circuitry in a circuit or a device according to the above embodiments and including software code portions for performing the method of any of the above method embodiments when the product is run on said processing circuitry.

BRIEF DESCRIPTION OF THE SEVERAL VIEWS OF THE DRAWINGS

One or more embodiments will now be described, by way of example only, with reference to the annexed figures, wherein:

FIG. 3A, FIG. 3B, FIG. 3C, and FIG. 3D are diagrams showing a gas sensor behavior in clean air and in the presence of a gas, FIG. 4 includes a plurality of diagrams showing a gas sensor behavior in different operating conditions and for different types of gases.

DETAILED DESCRIPTION

In the ensuing description, one or more specific details are illustrated, aimed at providing an in-depth understanding of examples of embodiments of this description. The embodiments may be obtained without one or more of the specific details, or with other methods, components, materials, etc. In other cases, known structures, materials, or operations are not illustrated or described in detail so that certain aspects of embodiments will not be obscured.

Reference to "an embodiment" or "one embodiment" in the framework of the present description is intended to indicate that a particular configuration, structure, or characteristic described in relation to the embodiment is comprised in at least one embodiment. Hence, phrases such as "in an embodiment" or "in one embodiment" that may be present in one or more points of the present description do not necessarily refer to one and the same embodiment. Moreover, particular conformations, structures, or characteristics may be combined in any adequate way in one or more embodiments.

The references used herein are provided merely for convenience and hence do not define the extent of protection or the scope of the embodiments.

Figure 1:
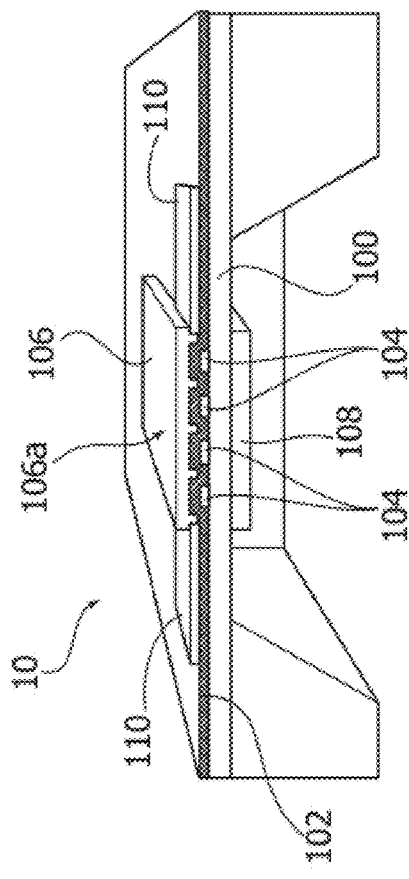
FIG. 1 shows a non-limiting example of a gas sensor according to one or more embodiments of the present disclosure.

FIG. 1 shows an example of a MOX-based gas sensor 10, e.g., comprising one or more gas sensing elements in MOX—metal oxide—technology, specifically a MOS—metal oxide semiconductor—technology. The sensor 10 may comprise:
- a micro-hot plate MHP formed by several elements illustrated in FIG. 1, as will be described in more detail below,
- a silicon substrate 108, and
- two electrodes 110, arranged substantially sidewise of the layer of metal oxide sensing material 106, e.g., on opposite lateral sides thereof.

In one or more embodiments, the micro-hot plate MHP may comprise a membrane 100, e.g., suspended in order to facilitate good thermal dissipation and isolation, a layer of electrical insulating material 102, e.g., alumina, and one or more heater elements 104 (e.g., platinum resistances) arranged thereon. Also, the micro-hot plate may comprise a layer of MOX sensing material 106 (e.g., tin dioxide—SnO2) arranged over the heater element(s) 104.

As exemplified in FIG. 1, the layer of electrical insulating material 102 of the micro-hot plate MHP may be arranged between the heater(s) 104 plus membrane 100 and the layer of MOX sensing material 106, with the MOX sensing material that may be provided onto the electrical insulating layer 102 by means of specific techniques, for example micro-dispensing or screen printing. Also, the heater(s) 104 may be sandwiched between the electrical insulating layer 102 and the membrane 100.

In one or more embodiments, the layer of MOX sensing material 106 may have a front surface 106a, opposite to a surface of the layer of MOX sensing material 106 facing towards the heater(s) 104, which may be exposed to air and may sense a target gas, e.g., a volatile organic compound VOC, if present.

As already discussed, the MOX conductance may change value proportionally to the VOC concentration at working temperatures. For example, the gas sensor 10 may provide a sensing signal, e.g., a resistance signal, that may be indicative of the presence of one or more gas target, wherein the resistance may decrease when the concentration of the target gas may increase.

In one or more embodiments, the VOC concentration may be calculated as a function of the variation of the MOX resistance signal in presence of a VOC with respect to the MOX resistance signal in clean air. A calibration of the MOX sensing material, at specific working conditions, may enable translation of this ratio into gas concentration (ppb, part per billion, or ppm, part per million).

In one or more embodiments, the two electrodes 110 may be placed onto the electrical insulating layer 102, at opposite lateral surfaces of the layer of MOX sensing material 106, with the two electrodes 110 electrically connected to the layer of MOX sensing material 106. The two electrodes 110 may be configured to obtain the MOX resistance value from the MOX sensing material 106 and, e.g., after calibration, such value may be converted in gas concentration.

In one or more embodiments, the heater(s) 104 are arranged below the layer of MOX sensing material 106 may allow to heat the layer of MOX sensing material 106 to one or more preferred working temperature values, for example between 350-400° C., and to maintain such values during operation of the sensor 10.

The micro-hot plate MHP may be cyclically (e.g., continuously) heated up to 450° C.: accordingly, the heated layer of MOX sensing material 106 may be reactive and sensitive to the presence of a target gas, e.g., volatile organic compounds VOC such as ethanol, toluene, benzene, formaldehyde. Intermittent heating of the micro-hot plate represents a conventional approach used for reducing the power consumption of the gas sensors: a micro-hot plate may be alternatively powered by a pulse switching on and off over time, i.e., a pulse switching between high and low values. A trade-off between level power consumption and performance (e.g., accuracy, sensitivity and stability) may be set for avoiding degradation of the gas sensor, e.g., by reducing the duty cycle and/or the current level.

Figure 2:
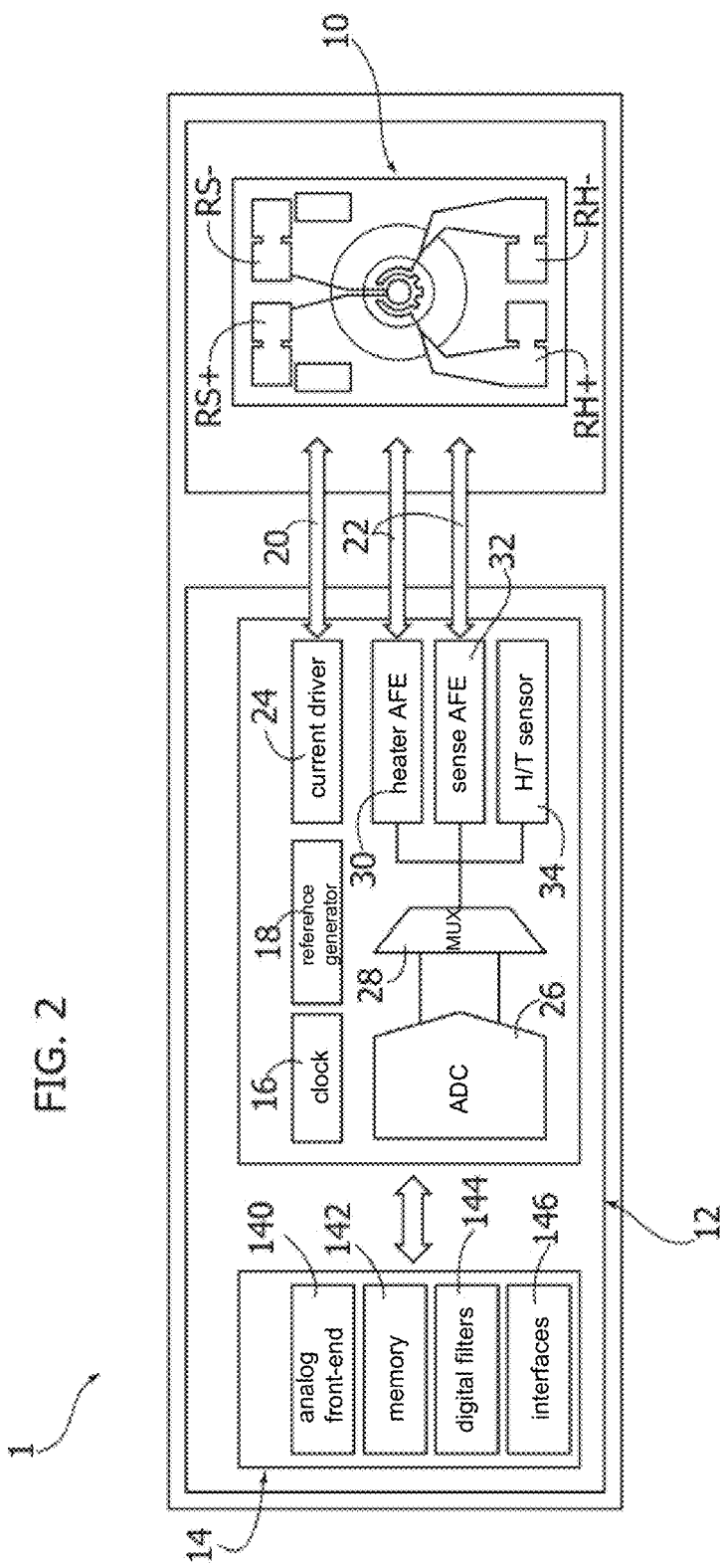
FIG. 2 shows a non-limiting example of a device including the gas sensor of FIG. 1 according to one or more embodiments.

As already discussed, one or more gas sensors 10 may be comprised in a portable device 1, exemplified in FIG. 2. The portable device 1 in FIG. 2 may comprise the sensor 10 and an (e.g., application-specific) integrated circuit 12, wherein the integrated circuit 12 is coupled to the sensor 10 and may be configured to perform the steps of the method according to one or more embodiments. The integrated circuit 12 may comprise a processor circuit 14 suited to be coupled to power nodes 20 and input nodes 22, and which can be configured to supply power to the sensor 10 (via nodes 20) and to receive (via nodes 22) signals indicative of an event produced by the sensor 10, e.g., for receiving the sensing data therefrom. Corresponding terminals may be found in the sensor 10: e.g., power terminals RH+, RH− and sensing terminals RS+, RS− to be connected to the power nodes 20 and input nodes 22 of the circuit according to one or more embodiments.

FIG. 2 shows various other elements which, in one or more embodiments, may be included in the circuit 12. For instance the processor circuit 14 may comprise a digital front-end, e.g., comprising a phase generator from the analog front-end 140, one or more memories 142, one or more digital filters 144 and one or more I2C/SPI interfaces 146.

In one or more embodiments, the circuit 12 may comprise further elements involved in operating the sensor 10. The following designations may apply to the blocks comprised in the integrated circuit 12:
- 16: clock;
- 18: reference current/voltage generator;
- 24: heater current driver;
- 26: analog-to-digital converter (ADC);
- 28: multiplexer;
- 30: heater analog front-end, AFE;
- 32: sense analog front-end, AFE; and
- 34: heater and humidity H/T sensor; this may be arranged in an opposite position of the device 1 with respect to the sensor 10, in order to facilitate avoiding interferences therewith.

In the following are indicated results obtained using a gas sensor arranged like the gas sensor in the device 1 of FIG. 2, in particular a ST GHT25S MOX gas sensor.

The indicated results are obtained with the following setup for conducting the experimental phase: a 90 liter Gas chamber is put into a climatic chamber with a reference probe for temperature and relative humidity such as the ROTRONIC hygroclip2 probe, a reference detector for VOC detection such as RaeGUARD2 PID (PhotoIonization Detector), and the integrated sensor circuit 20, in particular a ST GHT25S sensor. The ROTRONIC hygroclip2 probe is used as an additional reference tool for temperature and relative humidity measurements in the gas chamber, while the RAEGUARD2 PID is used for VOC concentration measurement in the gas chamber as well. The integrated sensor circuit 20 is driven according to different power profiles for generating characteristic patterns at different level of VOC concentrations by keeping constant the environmental conditions.

A heater current $I_h$, applied to the power terminals RH+, RH−, may be modulated in terms of envelope and/or period and/or baseline and/or amplitude. An example in presence of air of a sinusoidal current modulation of the heater current $I_h$ is reported in FIG. 3A, which report the sensor resistance R and the heater current $I_h$ as a function of time t. The heater current $I_h$ is sinusoidally modulated with a period of circa 12 s, and the sensor resistance R follows, in this case in presence of air substantially with an opposed phase, varying from 40KΩ to 365 KΩ following the level of the heater current $I_h$ driving the heating resistances 104.

It is underlined that in the example here discussed the heater current $I_h$ is not measured, the value shown is the value at which a current generator, e.g., the 2 heater current driver 24, present in the chip is set. Such current generator is digitally controlled by writing the current value in registers of the ASIC integrated in the device.

Thus, the heater current $I_h$ is a quantity which value is set or forced. It is possible to know its value by reading the abovementioned registers, then, for instance, reading the voltage drop measured on the heater 106 from other registers of the ASIC in which such measure is stored, and then obtaining the power dissipated by the heater and the heat which is generated by Joule effect by multiplying the heater current and heater voltage drop values in the ASIC registers. Then, to obtain from the generated heat, e.g., the heat applied to the sensor, to the actual temperature on the sensing element of the sensor requires the knowledge of a thermodynamic model, of thermal resistances, thermal exchange coefficients and other parameters of the sensor structure. Therefore preferably the measure of the heat applied is estimated by the heater current $I_h$ value which is set, e.g., the current generator is set to follow a sinusoidal modulation of the heater current $I_h$ value.

The current-temperature relation may be obtained by performing simulations, which allows estimating the temperature in stationary regime conditions for some heater current $I_h$ values.

As shown in the figures, the heater current Ih value is indicated in LSB (Less Significant Bit), which is the LSB of the value written in the register. For instance, after calibration, one LSB, i.e., the minimum current step which can be imposed on the heater 106, has a value of about 16 uA. Therefore, in the example here shown, the heater current Ih is modulated from a minimum of about 15 mA to a maximum of about 18 mA. It is clear that this pair of minimum and maximum values can vary depending on the device and the specific modulation parameters. In particular, the modulation parameters of mean value, amplitude and modulation period represent respective degrees of freedom of the system, which can be set to different values in order to drive differently the gas classification procedure.

In FIG. 3C the same diagram is shown in presence of acetone in the gas chamber, the variation of the sensor resistance R being from 1KΩ to 10 KΩ for the same range of variation of the driving current $I_h$ (15 mA-18 mA).

In FIGS. 3B and 3D it is shown the variation of the sensor resistance R versus the heater current $I_h$ in clean air and in presence of acetone. As shown the value of the gas sensor resistance R versus the variation of the driving heater current $I_h$ shows an hysteretic behavior, forming curves with closed hysteretic shapes P0, P1. Such formed shapes may be used as a base for extracting representative patterns that allow to identify one target gas from others by state-of-art expert systems or statistical techniques. In field conditions, the gas concentration changes continuously, the consequence being a continuous translation along the Z axis of the shapes of the $I_h$-R curves, although the three-dimensional object to which said $I_h$-R curves belong in itself maintains the same shape. Shapes formed in this kind of diagrams are connected to the chemical interaction of MOS sensing material type, its working temperature and the target gas.

Feature extraction and pattern recognition techniques based on Artificial Neural Networks have been used for classifying the shape of the R-$I_h$ curves and potentially they can be used for discovering the co-presence of multiple gases in the environment.

Figure 9:
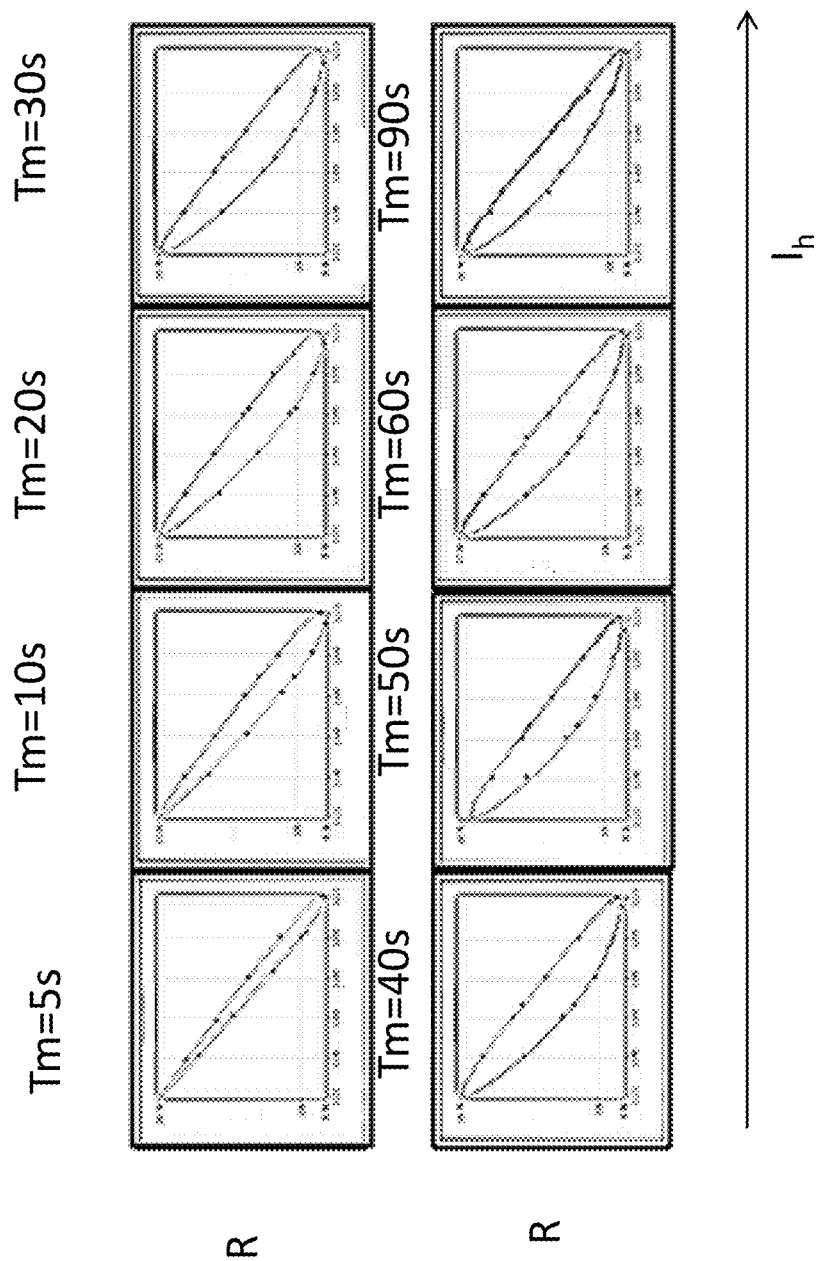
FIG. 9 illustrates a sensor state for clean air with different modulation periods.

In FIG. 9 it is shown a sensor state for clean air with eight different setting of sinusoidal modulation period $T_m$, from 5 to 90 s, and a high peak current $I_h$, e.g., that is 135% of baseline current level, which is the current level used during a standard measurement of resistance R (for instance in step 1002 in the following) while the low peak current is 95% of baseline current level. It can be seen that MOS temperature increasing and MOS temperature decreasing are followed by a quite symmetrical trend in terms of MOS resistance values.

Gases Isopropanol (G2), Ethanol (G3) Acetone (G1), and GPL (G4) have been used for evaluating the hysteresis behavior of the gas sensor resistance R during the driving current $I_h$ sweep.

Figure 4:
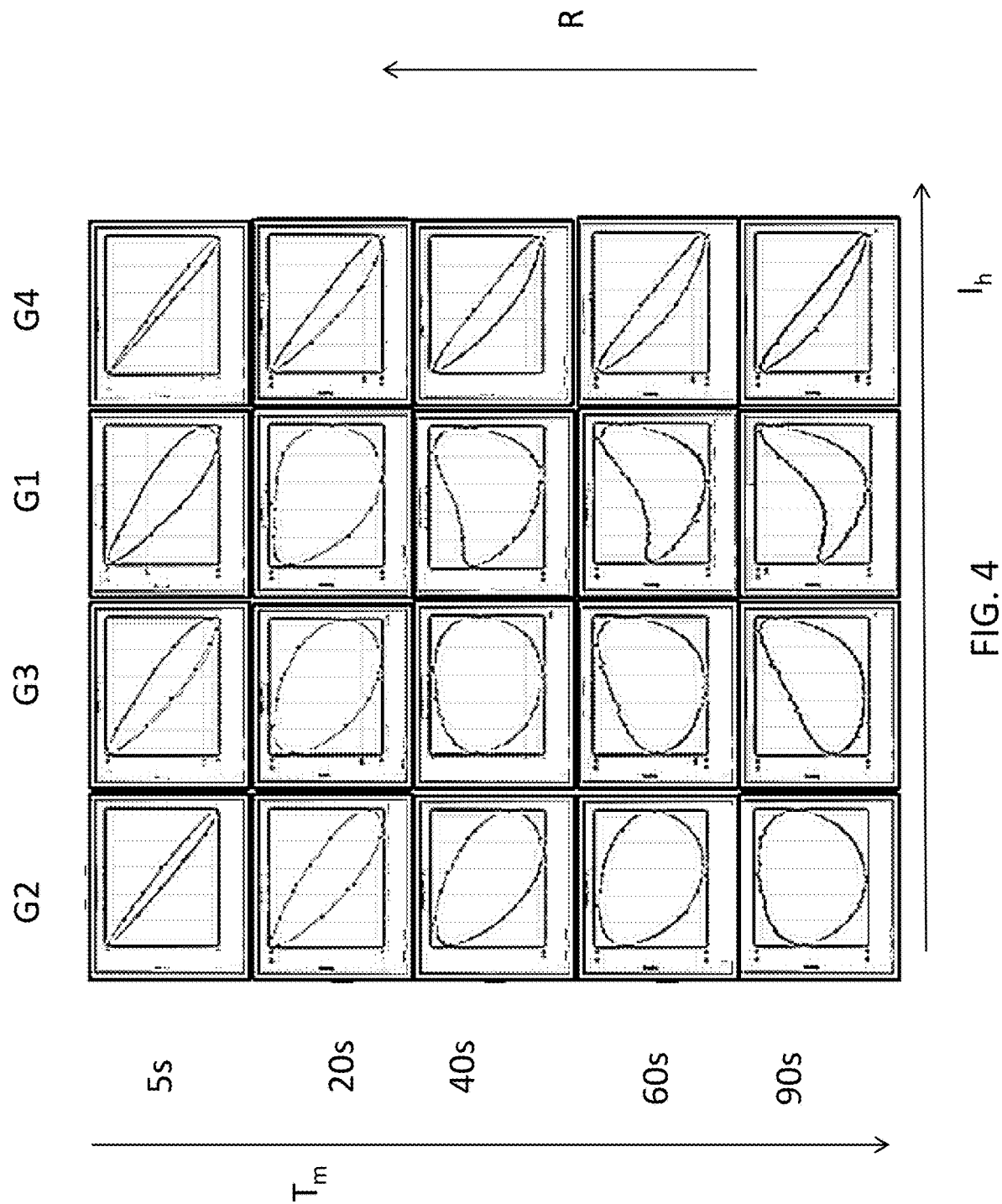

Thus, in FIG. 4 are shown diagram of gas sensor resistance R versus heater current $I_h$ for such gases. Each column of diagrams refers to a gas, i.e., Isopropanol G2, Ethanol G3 Acetone G1, and GPL G4 in that order, each row of diagrams corresponds to a different period $T_m$ of sinusoidal modulation, respectively 5 s, 20 s, 40 s, 60 s, 90 s. For each diagram, the range of variation of the heater current $I_h$ is the same, while the range of variation of sensor gas resistance R axis for each diagram varies between the minimum and maximum of measured value of the sensor gas resistance R, i.e., the axis is normalized to such minimum and maximum value, in order to show the shapes and the patterns of the hysteresis curves with roughly the same size.

As it can be seen, at a given value of sinusoidal period $T_m$, the patterns are quite different among the different gases G1, G2, G3, G4 and also have different evolution changing the value of the sinusoidal period $T_m$.

These different behaviors are known, and related according to different models to the interaction of the gas with the MOS active sensor, as described for instance in Manal Madhat Abdullah et al. "*Fabrication and Testing of SnO2, Thin Films as a Gas Sensor*," Applied Science Research, 2012, 4 (3):1279-1288 for Butane.

Shapes of curves as reported in FIG. 4 for different gases can be considered stabilized when they remain unmodified after a certain number of consecutive modulation cycles. As said above, patterns are generated from the shapes P traced by the measured values in the R-$I_h$ diagrams with the intent to recognize the target gas. They can be simply composed by an array of sensor resistance R values picked from the shapes P, possibly normalized to allow a better comparison, or by other parameters distinctive and characteristic of the curve R-$I_h$. The approach for recognizing pattern corresponding to the curve shapes P and thus the target gas G starting from such extracted patterns can be based on different statistical methods or alternatively on the use of expert systems.

For instance, a feedforward multilayer perceptron neural network can been applied for recognizing the pattern corresponding to the shapes of the curve of the MOS resistance R values sequence as extracted features from the hysteresis curve. Such Artificial Neural Network is formulated for instance with one hidden layer and trained by back propagation. The number of inputs is equal to the number of extracted features plus the MOS resistance $R_D$ value before starting the heater current modulation, which is indicated here as DC sensor resistance, i.e., corresponding to a constant level of heater current without modulation. The number of outputs is equal to the number of classes to be classified. The output represents belonging score to each target gas class. More in particular a likelihood value with respect to each class is obtained corresponding to a certain belonging score.

As mentioned also such signatures can be similar at different gas concentrations, even in case of different gases, and this can lead to misleading results, also using the above Artificial Neural Network.

Therefore, to enhance the selectivity of a gas sensor, in particular a metal oxide gas sensor, when the gas concentration changes, e.g., in field conditions, it is here described a method of operating a gas sensor, enhancing the selectivity of such gas sensor, in particular Metal Oxide gas sensor, including applying heat by a heater to a metal oxide sensing element of a gas sensor and measuring at least an electrical resistance of said metal oxide sensing element of the gas sensor versus a variation of the heat applied to the metal oxide sensing element, comparing said measurement of at least the electrical resistance of said metal oxide sensing element versus said variation of the heat applied to the metal oxide sensing element to corresponding reference measurements associated with a plurality of different target gases, wherein said measuring step includes measuring a further sensor parameter versus the variation of said electrical resistance of said metal oxide sensing element of the gas sensor and said heat applied to the metal oxide sensing element obtaining a trajectory in three dimensions corresponding to the variation of said sensor resistance, said heat and said further sensor parameter, said comparing said measurement includes comparing said trajectory to one or more reference three-dimensional objects in said three dimensions corresponding to the variation of said sensor resistance, said heat and said further sensor parameter associated with a plurality of different target gases.

Such a method allows building up a more powerful tool for identifying and recognizing the VOC family or type.

The solution proposed regards a method and an operating mode that provides a more robust classification, in particular obtaining a trajectory in a three-dimensional space which dimensions are preferably the sensed gas sensor resistance R, the heating current $I_h$ and a DC resistance, i.e., the MOS resistance R value before starting the modulation, $R_D$, the signature being also indicated as R2C (Resistance-Resistance-Current). Such trajectory is compared to a three-dimensional object SS, which can be a three-dimensional volume or a three-dimensional surface, in a three-dimensional diagram where the x-axis reports the MOX Resistance in AC modulation, e.g., the gas sensor resistance R, the y-axis reports the heater driving current $I_h$ and, finally, the z-axis reports the MOX Resistance in DC, $R_D$. The status of the gas sensor is represented by a point, i.e., a triplet (R, $I_h$, $R_D$) on the surface of such three-dimensional object SS.

Such three-dimensional object SS is constructed in a characterization phase, e.g., at the factory, where the resistance of the gas sensor 10 is measured at different levels of concentration at the selected operating conditions, e.g., value of heating current $I_h$. Changing the operating condition, the shape of the three-dimensional object SS changes accordingly. Changing the heating current $I_h$ and thus the temperature of the heater, specifically the micro hot plate MHP, for a defined level of gas concentration, the points representing the gas sensor status, which, as mentioned, are a triplet of values $I_h$, R, $R_D$, form a trajectory corresponding to a section of the three-dimensional object at the corresponding $R_D$ value on the z-axis, e.g., corresponding to the current gas concentration. The DC sensor resistance $R_D$ is converted in ppm of gas concentration according to the calibration data generated at factory level.

Figure 5B:
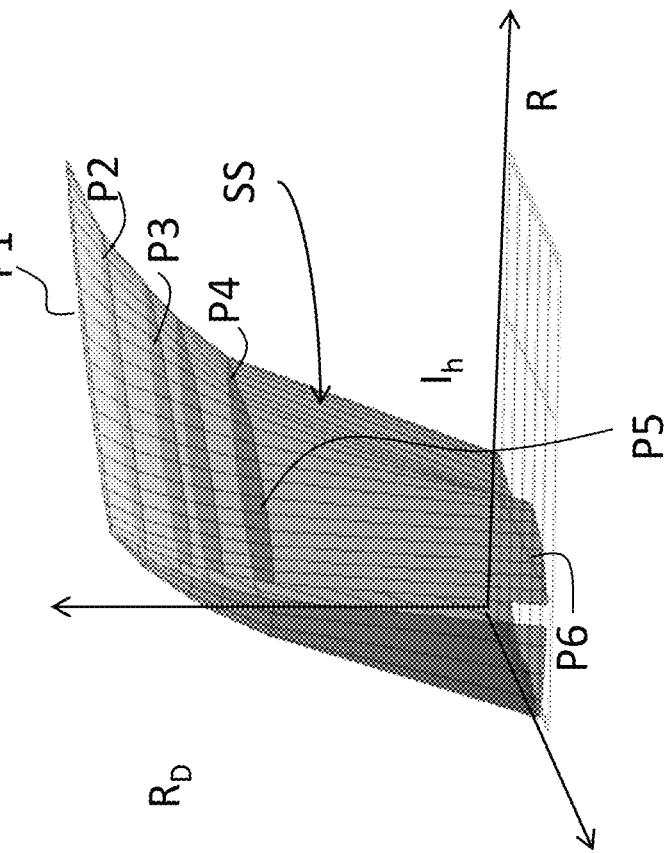
FIGS. 5A and 5B are a non-limiting example of diagrams illustrative of the construction of a three-dimensional object used by steps of a method according to one or more embodiments.
Figure 5A:
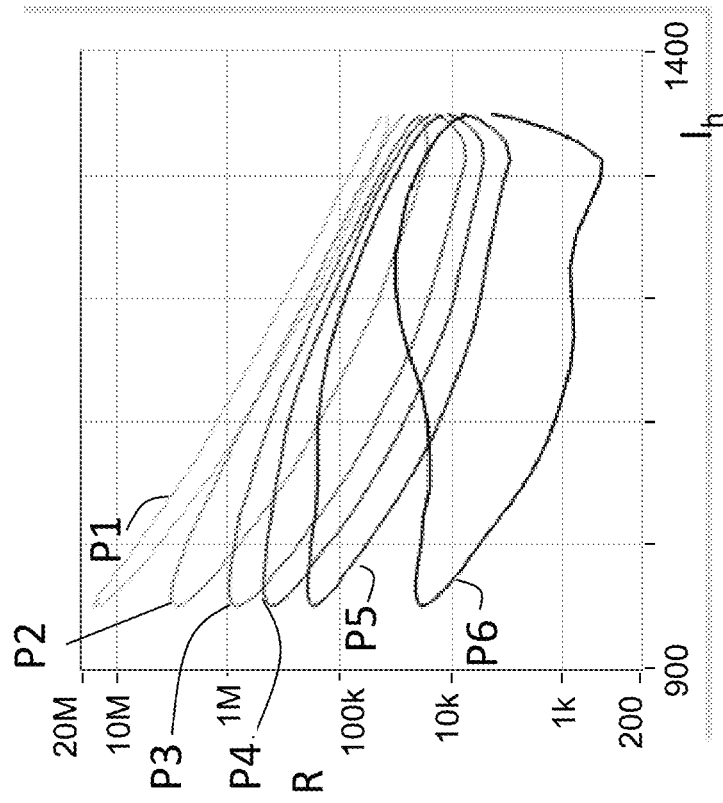

In FIGS. 5A-5B is represented an example of a three-dimensional object SS, which uses the sensor resistance R, which is calculated in AC modulation, the heating current $I_h$ and a DC resistance $R_D$.

Figure 6A:
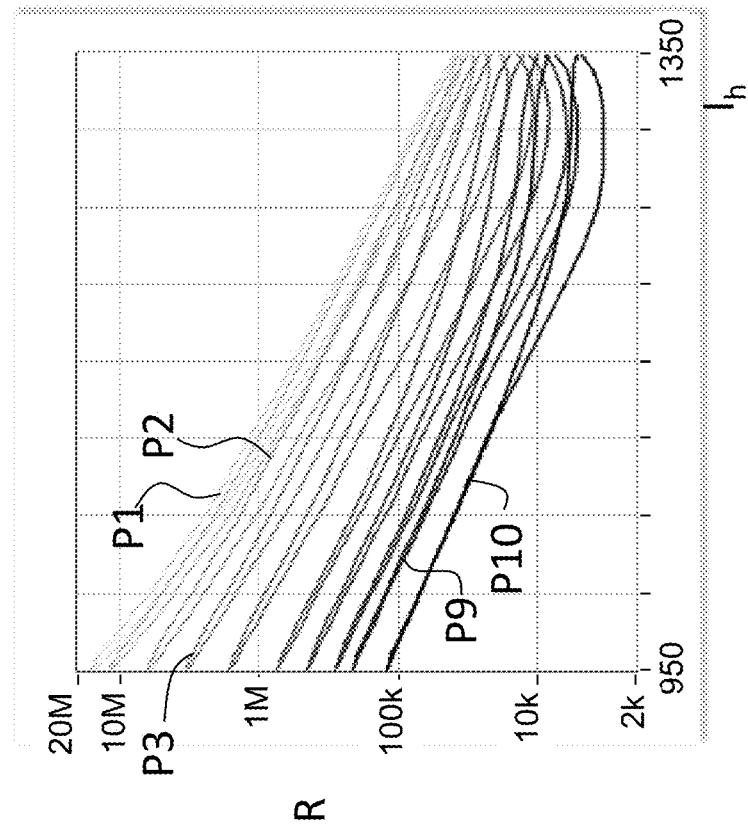
FIGS. 6A and 6B represent a further non-limiting example of diagrams illustrative of the construction of a three-dimensional object used by steps of a method according to one or more embodiments.
Figure 6B:
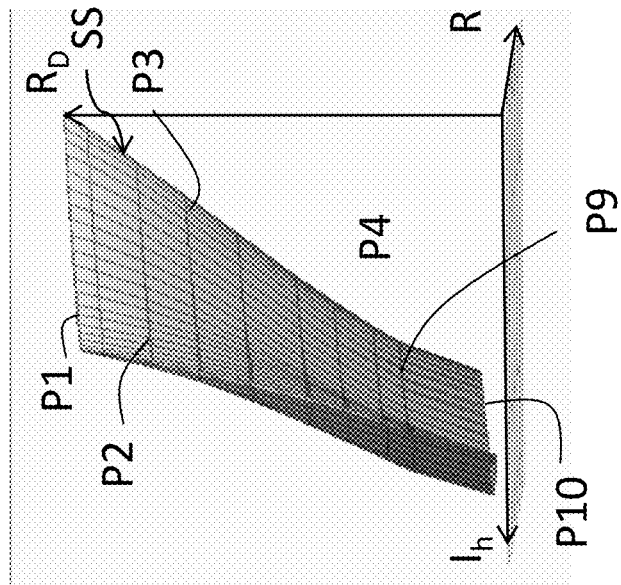

In FIG. 5A is shown a bi-dimensional diagram, for gas Acetone, charting the sensor resistance R versus the heating current $I_h$. The concentration of Acetone is changed from high to low concentrations till to reach a clean air state, and evolution on time of the shapes P in the plane $I_h$-R are observed by considering the progressive reduction of VOC concentration till clean air. In particular six shapes are shown from P1, corresponding to the highest Acetone concentration, to P6, clean air. FIG. 5A shows the shapes evolution, while FIG. 5B reports a three-dimensional representation of the shapes P1-P6 where the z-axis is the MOS resistance value before starting the modulation (DC mode), e.g., $R_D$. It represents the ppm level based on an integrated sensor circuit 10 calibration at factory level. In FIG. 5B it is shown also the three dimensional object, or solid shape, SS which is the envelope of the shape P1-P6. Shape P1 at maximum MOS resistance value $R_D$ represents the shape in the clean air condition. In short, shapes evolution is gas depending and trend towards to the clean air shapes. In FIG. 6A-6B the same diagrams are reported for GPL. The different 2D shapes for different gas concentration are in this case ten, from P1 to P10 (only some of them are captioned, for simplicity's sake), P1 representing the clean air condition.

Of course, the solid shapes SS of FIGS. 5B and 6B can be observed by different point of view.

As shown in FIG. 4, a longer modulation period Tm allows to obtain curves P with more distinctive shapes. However, a shorter modulation period helps to maintain the stationarity of the gas concentration, which as shown in the following FIGS. 5 and 6 is a condition in which the curves P forming the three dimensional objects SS are substantially parallel to the $I_h$-R plane. In an embodiment modulation period Tm may be maintained between 10 and 20 s.

Figure 7:
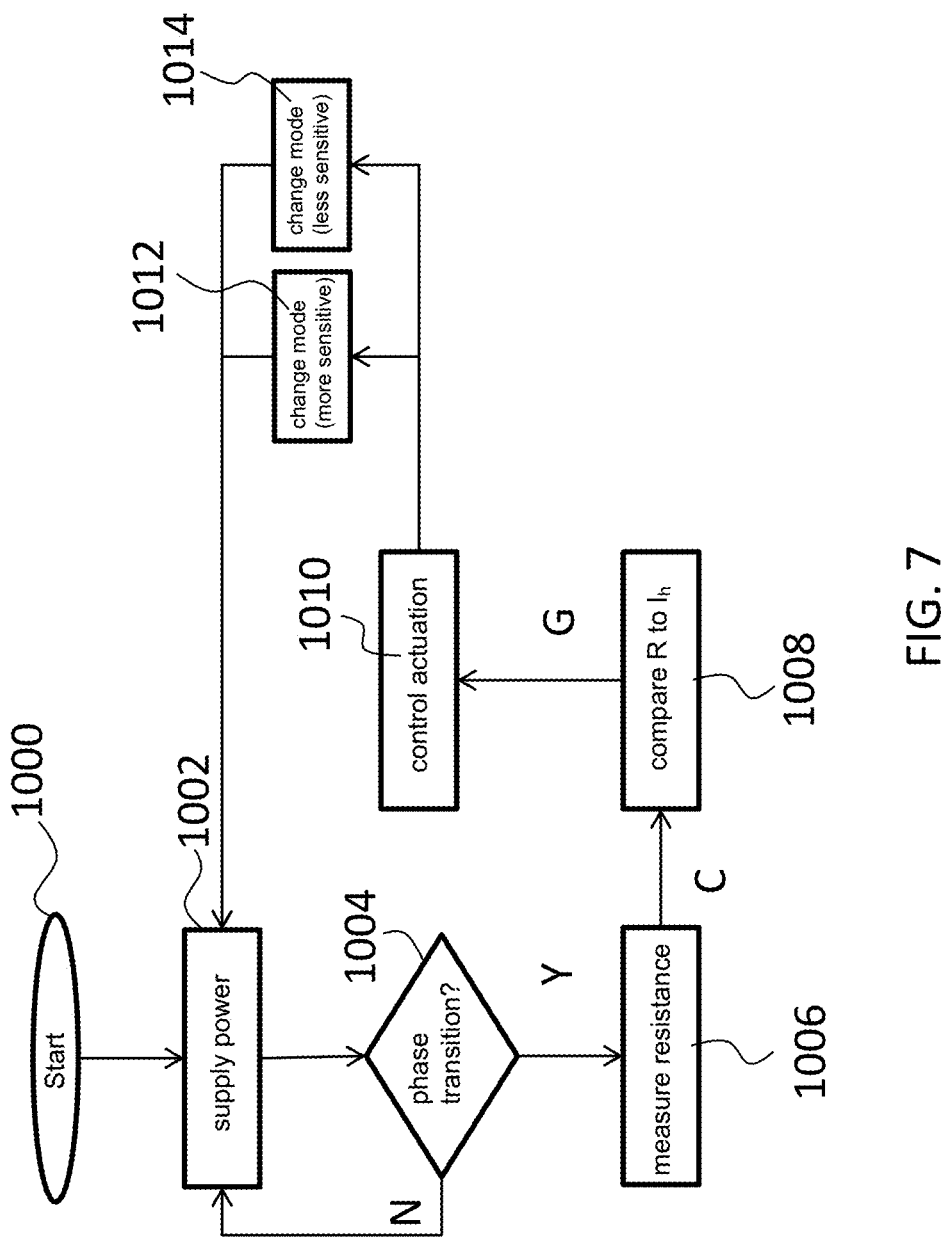
FIG. 7 is a flow chart showing a non-limiting example the steps of a method according to one or more embodiments.
Figure 8:
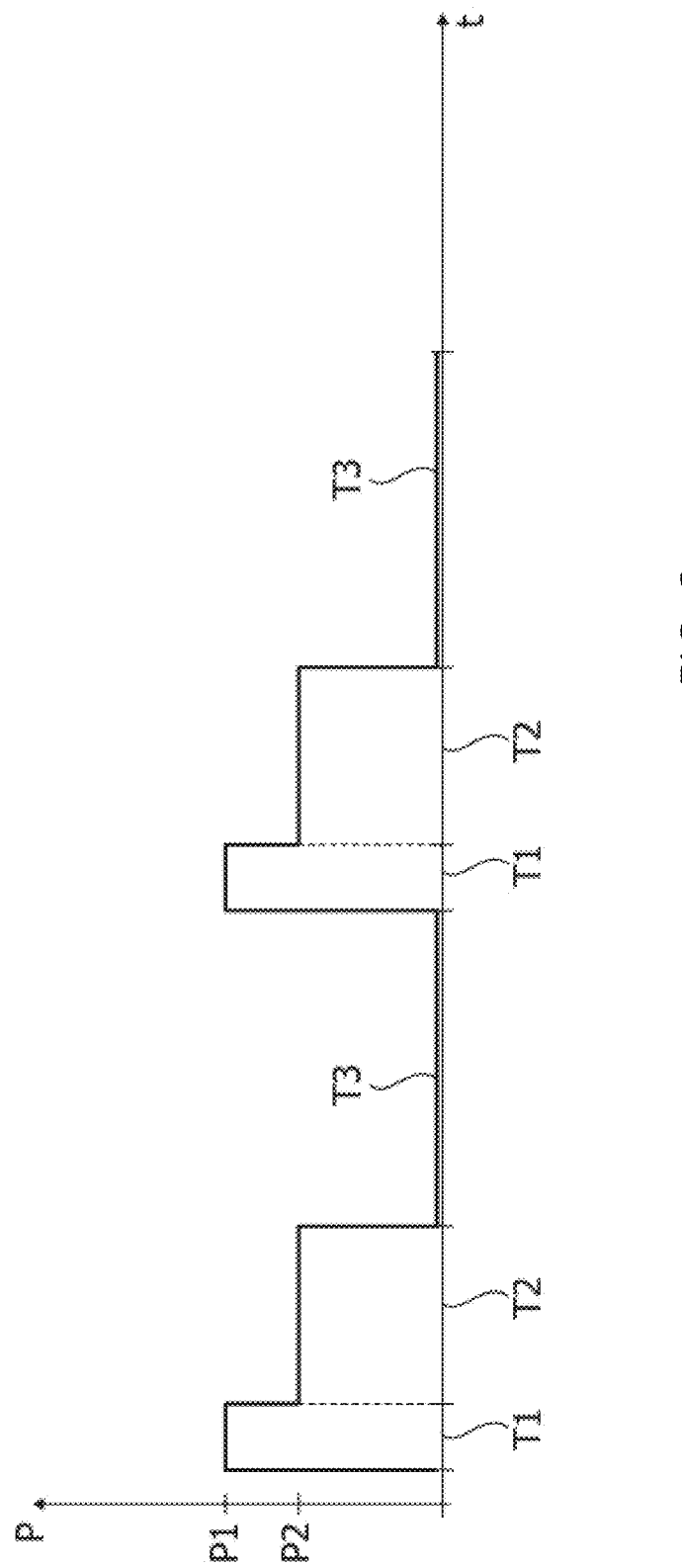
FIG. 8 is a signal diagram showing a non-limiting example of possible driving profile for a gas sensor according to one or more embodiments.

In FIG. 7 it is shown a flow diagram representative of an embodiment of a method for operating the gas sensor according to the solution here described, in particular by operating a VOC recognition using shapes of characteristic three-dimensional objects SS.

With reference to FIG. 7, after the sensor 10 is switched on (start step 1000), the sensor 10 may operate in a normal mode comprising supplying power (1002) to the sensor 10 according to a normal power profile. For example, the normal mode may comprise a pulsed mode or a continuous mode, or may comprise different current profiles for heating the micro-hot plate MHP. An intermittent heating profile may be used as the normal power profile, wherein each cycle may comprise:

- a first power value P1 applied to the sensor 10 for a first time interval T1 (e.g., 0.5 s),
- a second power value P2, different from (e.g., smaller than) the first power value P1, applied to the sensor 10 for a second time interval T2 (e.g., 4.5 s), the second time interval T2 being different from (e.g., longer than) the first time interval T1, and
- no power applied to the sensor 10 for a third time interval T3 (e.g., 55 s) that may be longer than the first and second time interval T1 and T2.

It will be otherwise understood that the power profile exemplified herein may vary even significantly, insofar as the normal mode power profile may depend on the MOX-based gas sensor 10 employed and the application specific constraints. For example, the normal power profile may be modified based on the gas sensor 10 employed to obtain a trade-off between sensitivity performance plus time response and power consumption.

In one or more embodiments, during normal mode, the sensor 10 may thus be operated with the normal power profile (1002), heating the Micro-Hot-Plate MHP in order to have the target performance (sensitivity, response time) vs power consumption.

The gas concentration is calculated on the basis of the gas sensor resistance value R during heating. The gas concentration (ppm level) is computed by converting the MOX resistance value in ppm by means of individual calibration curves built at factory level.

Then in a step 1004 a transition check is performed, to check if a transition from a stationary regime or phase to another has taken place, this being for instance representative of a variation in gas concentration.

The feature exploited is a slope SL of gas sensor resistance R according to the driving mode.

The transition check 1004 is based on the following condition, here below expressed in logic form:

```
IF ( abs(SL) > TH_SL1 )
    TP = TRUE
    SP = FALSE
IF ( (TP = TRUE) & ( abs(SL) < TH_SL2 ) )
    TP = FALSE
    SP = TRUE
    IF ( abs(log(MM / R_D)) > TH_RD )
        TR = TRUE
    ELSE
        TR = FALSE
```

$R_D$=MM where:
- SL is the slope of the gas sensor resistance R as a function of time.
- TH_SL1 is a threshold for a transient phase TP;
- TH_SL2 is a threshold for a stationary phase SP;
- TH_RD is a threshold for RD variation;
- $R_S$ is the measured resistance value in the gas sensor;
- $R_D$ is the value of the DC resistance;
- MM is a variable storing the value of the last DC resistance
- TR is a flag for transition signaling.

In other word the check operation 1004 in the first place checks if the slope SL indicating the variation of the gas sensor resistance R in time is greater than the first threshold TH_SL1. If this is true, the quick change, in particular drop, of the gas sensor resistance R in time is considered as representing the transient phase TP. Such change is not necessarily a drop, also an increase of the sensor resistance R can be considered as representative of a transition from a stationary phase, following which it is possible to apply the heat or temperature modulation. To apply the heat modulation, however, it is needed to reach a new stationary phase SP, i.e., the transient phase TP has to be finished. Thus, subsequently, if the sensor 10 is in a transient phase TP and the slope SL is lower than the second threshold TH_SL2 for a stationary phase SP, this condition is indicated as representative of the new stationary phase SP.

Then, to validate the occurring of a transient phase TP, preferably it is also checked, in addition to the variation of the slope SL, also that there is a significant variation of the sensor resistance R in the new stationary phase with respect to the resistance $R_D$ in the previous stationary state (stored in the variable MM). This control is performed by computing a ratio of the two resistances and comparing it to a threshold for RD variation, TH_RD, in particular as shown is evaluated if (abs(log(MM/$R_D$))>TH_RD). Flag TR is set to TRUE if both conditions are true a) stationary regime after a transient; b) significant DC resistance variation.

The gas sensor works in normal mode, i.e., performing operation 1002, and check continuously (1004) if the MOX resistance R is changing due to the presence of some VOC in the environment.

If the check 1004 is positive, an operation 1006 of measurement of a three-dimensional hysteretic trajectory C is performed in the $I_h$-R-$R_D$ three-dimensional space, measuring the sensor gas resistance R varying the heating current $I_h$.

In an embodiment of operation 1006, such operation may include a first step of acquisition of the DC resistance $R_D$ (which corresponds to the gas concentration in ppm according to a conversion factor set in the factory). Then operation 1006 may include a step in which the gas sensor resistance R versus the variation of heating current $I_h$, in the embodiment a sinusoidal modulation is measured and the corresponding three-dimensional hysteretic trajectory C acquired.

Thus, in one or more embodiment, the method here described includes the operation 1006 of measurement of a three-dimensional hysteretic trajectory C which includes a step of acquisition of the sensor resistance R measured before applying said modulation as further sensor parameter $R_D$ and a step in which the gas sensor resistance R versus the variation of heating current $I_h$ is acquired, the resistance R of the metal oxide sensing element 106 of the gas sensor 10 versus a variation of the heating current $I_h$ be obtained by modulating said heat in time t and the further sensor parameter $R_D$ being a sensor resistance measured before applying said modulation, i.e., before the time interval, which may correspond for instance to at least a modulation period $T_m$, of application of said variation or modulation of the heating current $I_h$ and consequently of the heat applied to the metal oxide sensing element 106 of the gas sensor 10.

Then a step of classification 1008 by statistical or expert systems is performed on the three-dimensional trajectory C obtained at step 1006. Time-domain or frequency-domain features of the curve C can be extracted with the purpose of recognizing the VOC family or type by means of statistical methods or expert systems. For instance, an expert system can be trained for recognizing a trajectory C on the surface of the three-dimensional object SS (3D signature).

As mentioned, a feedforward multilayer perceptron neural network can been applied for recognizing the pattern corresponding to the shapes of the curve of the MOS resistance R values sequence as extracted features from the hysteresis curve. Such Artificial Neural Network is formulated for instance with one hidden layer and trained by back propagation. The number of inputs is equal to the number of extracted features plus the MOS resistance R value before starting the modulation, e.g., DC resistance $R_D$. The number of outputs is equal to the number of classes to be classified. The output represents belonging score to each target gas class.

The reference three-dimensional object SS, as mentioned, can be by a previous characterization phase where the resistance R of the gas sensor 10 is measured at different levels of concentration at selected operating conditions. One or more of such reference three-dimensional object SS, corresponding to different gases, may be stored in a memory of the integrated circuit 12.

The step of classification 1008 performs the classification, e.g., recognition of the target gas G. More in detail, in an embodiment the classification 1008 may produce a classification rate, i.e., a recognition probability, which is then analyzed to perform a final evaluation.

Once the target gas G is recognized, a step 1010 of controlling an actuation system (not shown in the figures) may be performed according to the use case. For instance the air conditioning system can be actuated (opening or closing valves, . . . ) if a given gas G is identified.

Also it is indicated a step 1012 in which the gas sensor 10 can be driven for changing the operating mode in order to be more sensitive to the detected gas G.

Also it is indicated a step 1014 in which the gas sensor 10 can be driven for changing the operating mode in order to be less sensitive to the detected gas G.

After a time-out or when some additional conditions are verified the gas sensor can return to the standard operating mode, e.g., to step 1002.

On the basis of what has been described with reference to FIG. 7, thus in one or more embodiments the method here described may include measuring 1002 a gas sensor resistance R,
checking 1004 the presence of a gas by measuring a variation in time of said gas sensor resistance R,
when variation in time of said gas sensor resistance matches a stationarity criterion,
performing at least said operation 1006 of measurement of a three-dimensional hysteretic trajectory C and said comparing operation 1008.

Without prejudice to the underlying principles, the details and embodiments may vary, even significantly, with respect to what has been disclosed by way of example only, without departing from the extent of protection.

The extent of protection is defined by the annexed claims.

The solution described relates to a method for enhancing MOX gas sensor selectivity to target gases such as benzene, methane, and ethanol and other volatile organic compound. The application is in the field of handled devices or wearable devices where the demand is to be featured with attributes of low-power and low latency. This solution can be applied in user contexts like home and general indoor environment, car and general vehicle cockpits. The solution described is applicable to the field of environmental sensors for mobile, handled and wearable devices in the consumer, automotive and industrial markets.

Other parameters different from the DC resistance can be used as third dimension of the three dimensional space in which the three dimensional trajectory and reference three dimensional object are measured. For instance any other parameter representing the gas concentration may be used.

The various embodiments described above can be combined to provide further embodiments. All of the U.S. patents, U.S. patent application publications, U.S. patent applications, foreign patents, foreign patent applications and non-patent publications referred to in this specification and/ or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method, comprising:
applying heat by a heater to a metal oxide sensing element of a gas sensor by applying a heating current to the heater;
detecting, by the gas sensor, a presence of a target gas;
measuring, in response to detecting the presence of the target gas, first electrical resistance of said metal oxide sensing element of the gas sensor in a first time interval in which the heat applied to the metal oxide sensing element is modulated;
measuring, in response to detecting the presence of the target gas, second electrical resistance of said metal oxide sensing element of the gas sensor in a second time interval in which the heat applied to the metal oxide sensing element is constant without modulation;
obtaining a trajectory of the target gas in three dimensions having a first axis corresponding to the first electrical resistance, a second axis corresponding to the heating current, and a third axis corresponding to the second electrical resistance; and
recognizing the target gas by comparing said trajectory in the three dimensions to a set of reference three-dimensional objects that are each represented according to the three dimensions and that are associated with a plurality of different target gases, respectively.

2. The method of claim 1, wherein the second electrical resistance is proportional to a gas concentration.

3. The method of claim 1, wherein the second time interval is before the first time interval.

4. The method of claim 1, wherein the modulation of the heat in the first time interval includes a sinusoidal modulation of the heat in the first time interval.

5. The method of claim 1, wherein said set of reference three-dimensional objects are obtained by a previous characterization phase comprising measuring the first electrical resistance of the gas sensor at different levels of concentration at selected operating conditions.

6. The method of claim 1, wherein said comparing said trajectory in the three dimensions to the set of reference three-dimensional objects comprises recognizing said trajectory on a surface of one of the three-dimensional objects in the set of reference three-dimensional objects.

7. The method of claim 6, wherein comparing said trajectory comprises comparing said trajectory through at least one of statistical methods, an expert system, or an Artificial Neural Network.

8. The method of claim 1, further comprising:
measuring a gas sensor resistance;
measuring a variation in time of said gas sensor resistance; and
when a variation in time of said gas sensor resistance identifies a transient phase and a subsequent new stationary phase representative of a change in gas concentration, performing at least measuring said trajectory and comparing said trajectory in three dimensions to the set of reference three-dimensional objects.

9. The method of claim 8, further comprising checking if the variation in time of the gas sensor resistance in the subsequent new stationary phase with respect to a previous stationary phase is greater than a given value.

10. The method of claim 1, further comprising controlling an actuation system based on the recognized target gas.

11. The method of claim 1, further comprising at least one of:
driving the gas sensor in order to make the gas sensor be more sensitive to the recognized target gas; or
driving the gas sensor in order to make the gas sensor be less sensitive to the recognized target gas.

12. The method of claim 1 wherein the heating current is an alternating current in the first time interval, and is a direct current in the second time interval.

13. A device, comprising:
a sensor including a sensing element configured to produce a sensing signal indicative of a target gas, and including a first power node to receive electrical power; and
a circuit including:
an input node coupled to the sensor to receive the sensing signal;
a second power node coupled to the first power node of the sensor; and
processing circuitry coupled to the input node and the second power node, the processing circuitry configured to:
apply current to the second power node to generate heat that is applied to the sensing element;
detect a presence of the target gas based on the sensing signal;
measure, in response to detecting the presence of the target gas, first electrical resistance of the sensing element in a first time interval in which the heat applied to the sensing element is modulated;
measure, in response to detecting the presence of the target gas, second electrical resistance of the sensing element in a second time interval in which the heat applied to the sensing element is constant without modulation;
obtain a trajectory of the target gas in three dimensions having a first axis corresponding the first electrical resistance, a second axis corresponding to the current, and a third axis corresponding to the second electrical resistance;
recognize the target gas by comparing said trajectory in the three dimensions to a set of reference three-dimensional objects that are each represented according to the three dimensions and that are associated with a plurality of different target gases, respectively.

14. The device of claim 13, wherein the second electrical resistance is proportional a concentration of a gas in which the sensor is present.

15. The device of claim 13, wherein the modulation of the heat in the first time interval includes a sinusoidal modulation of the heat applied to the sensing element in the first time interval.

16. The device of claim 13, wherein the processing circuitry is configured to execute an Artificial Neural Network.

17. A computer program product, loadable in a memory of processing circuitry, the computer program product including software code portions which, when the computer program product is executed on the processing circuitry, cause the processing circuitry to carry out the operations of:
applying heat by a heater to a metal oxide sensing element of a gas sensor by applying a heating current to the heater;
detecting, by the gas sensor, a presence of a target gas;
measuring, in response to detecting the presence of the target gas, first electrical resistance of said metal oxide sensing element of the gas sensor in a first time interval in which the heat applied to the metal oxide sensing element is modulated;
measuring, in response to detecting the presence of the target gas, second electrical resistance of said metal oxide sensing element of the gas sensor in a second time interval in which the heat applied to the metal oxide sensing element is constant without modulation;
obtaining a trajectory of the target gas in three dimensions having a first axis corresponding to the first electrical resistance, a second axis corresponding to the heating current, and a third axis corresponding to the second electrical resistance; and
recognizing the target gas by comparing said trajectory in the three dimensions to a set of reference three-dimensional objects that are each represented according to the three dimensions and that are associated with a plurality of different target gases, respectively.

18. The computer program product of claim 17, wherein the second electrical resistance is proportional to a gas concentration in which the gas sensor is immersed.

19. The computer program product of claim 17, wherein the second time interval is before the first time interval.

20. The computer program product of claim 17, wherein the heat applied the metal oxide sensing element in the first time interval is modulated by sinusoidally modulating the heat in the first time interval.

21. The computer program product of claim 17, wherein the computer program product further includes software code portions which, when the computer program product is executed on the processing circuitry, cause the processing circuitry to carry out:
driving the gas sensor to make the gas sensor more sensitive to the recognized target gas; or
driving the gas sensor to make the gas sensor less sensitive to the recognized target gas.

* * * * *